United States Patent [19]

Merianos et al.

[11] Patent Number: 5,066,488
[45] Date of Patent: Nov. 19, 1991

[54] SEMI-ANHYDROUS, SUSPENSION PROCESS FOR PREPARING UNIFORM, FREE-FLOWING, FINE, WHITE POWDERS OF SUBSTANTIALLY ANHYDROUS COMPLEXES OF PVP AND $H_2O_2$ CONTAINING ABOUT 18 TO ABOUT 22% $H_2O_2$

[75] Inventors: John J. Merianos, Middletown; Robert B. Login, Oakland; Paul Garelick, South Plainfield, all of N.J.

[73] Assignee: ISP Investments Inc., Wilmington, Del.

[21] Appl. No.: 533,749

[22] Filed: Jun. 6, 1990

Related U.S. Application Data

[62] Division of Ser. No. 278,342, Dec. 1, 1988, Pat. No. 4,948,823.

[51] Int. Cl.$^5$ ............................................. A61K 31/785
[52] U.S. Cl. ....................................... 424/80; 424/486
[58] Field of Search ........................... 424/80, 486, 613

[56] References Cited

U.S. PATENT DOCUMENTS 3,480,557 11/1969 Shiraeff ..................... 252/186
3,755,185 8/1973 Waldmann et al. ................. 252/186

Primary Examiner—Thurman K. Page
Assistant Examiner—P. Kulkosky
Attorney, Agent, or Firm—Walter Katz; Marilyn J. Maue; Joshua J. Ward

[57] ABSTRACT

What is provided herein is a semi-anhydrous, suspension process for preparing substantially anhydrous complexes of PVP and $H_2O_2$ containing about 18% to about 22% by weight $H_2O_2$. The process comprises suspending substantially anhydrous PVP and an aqueous solution of 70 to 85% $H_2O_2$ in an anhydrous ethyl acetate medium to precipitate a free-flowing, fine white powders of the complex, and filtering and drying under vacuum at about 40°–50° C. to form the desired product.

6 Claims, No Drawings

SEMI-ANHYDROUS, SUSPENSION PROCESS FOR PREPARING UNIFORM, FREE-FLOWING, FINE, WHITE POWDERS OF SUBSTANTIALLY ANHYDROUS COMPLEXES OF PVP AND $H_2O_2$ CONTAINING ABOUT 18 TO ABOUT 22% $H_2O_2$

CROSS-REFERENCE TO RELATED PATENT APPLICATIONS

This is a division of application Ser. No. 278,342 filed Dec. 1, 1988, now U.S. Pat. No. 4,948,823.

Copending U.S. patent application, Ser. No. 434,943, filed Nov. 8, 1989,U.S. Pat. No. 5,008,093 describes an anhydrous process for the preparation of substantially anhydrous complexes of PVP and $H_2O_2$ by reacting PVP and $H_2O_2$ in suspension in an anhydrous ethyl acetate organic solvent.

BACKGROUND OF THE INVENTION

1. Field of the Invention

This invention relates to substantially anhydrous complexes of polyvinylpyrrolidone (PVP) and hydrogen peroxide ($H_2O_2$), and, more particularly, to a semi-anhydrous, suspension process for preparing such stabilized complexes as uniform, free-flowing, fine, white powders containing about 18 to about 22% $H_2O_2$.

2. Description of the Prior Art

In the copending U.S. patent application, water soluble or insoluble PVP powder containing about 4.5% water is suspended in anhydrous ethyl acetate and an anhydrous $H_2O_2$ solution in ethyl acetate is added thereto. Upon mixing, a fine, white powder is obtained, which is filtered and dried in vacuo to remove residual solvent. The product is a stable, substantially anhydrous complex of PVP and $H_2O_2$ in the form of a uniform, free-flowing, fine white powder having an $H_2O_2$ content between about 13% and 23%. This process, however, requires the use of anhydrous $H_2O_2$ in ethyl acetate which is difficult to prepare and to handle safely.

Shiraeff, in U.S. Pat. Nos. 3,376,110 and 3,480,557, discloses a solid, stabilized hydrogen peroxide composition of hydrogen peroxide and a polymeric N-vinyl heterocyclic compound prepared in an aqueous solution of the components. These compositions generally were prepared by mixing various weights of PVP and aqueous $H_2O_2$, and evaporating the solution to dryness. The Shiraeff composition, which was believed to be a solid, dry complex, was described as not necessarily anhydrous due to the hydrophilic nature of the PVP and the water present in the reaction solution. Shiraeff further stated that such amounts of water could be tolerated, however, if it did not affect the solid dry characteristics of the complexes. The $H_2O_2$ content of the composition was given as being at least 2%, and preferably 4.5 to 70% by weight. Prolonged drying to remove water from such compositions, however, resulted in loss of $H_2O_2$ forming a brittle, transparent, gummy, amorphous product. In U.S. Pat. No. 3,480,557, the aqueous PVP-$H_2O_2$ complexes, upon heating to dryness, produced hard, brittle chips which had a variable $H_2O_2$ content ranging from about 3.20 to 18.07% by weight, depending upon the drying times.

Accordingly, it is an object of this invention to provide a process of making stabilized, substantially anhydrous complexes of PVP and $H_2O_2$ as a uniform, free-flowing, fine, white powder containing about 13 to 23% $H_2O_2$ which does not require the use of anhydrous $H_2O_2$ solutions.

A particular object herein is to provide a suspension process using only 70–85% $H_2O_2$ aqueous solutions for making substantially anhydrous, uniform, free-flowing, fine, white powder complexes of PVP and $H_2O_2$ having a $H_2O_2$ content between about 18 to about 22%.

SUMMARY OF THE INVENTION

What is provided herein are uniform, fine, white powders of substantially anhydrous complexes of PVP and $H_2O_2$ containing about 13% to about 22% by weight $H_2O_2$ which are prepared by reaction between substantially anhydrous water-insoluble PVP and a 70% to 85% aqueous $H_2O_2$ solution, in a suspension in anhydrous ethyl acetate. The product is obtained as a fine, white precipitate which is dried at about 40°–50° C. in vacuo for a predetermined period of time.

The filtrate from the above process can be recycled into the process.

DETAILED DESCRIPTION OF THE INVENTION

In the suspension process of the present invention, the water-insoluble PVP polymeric starting material is available commercially as a solid of varying molecular weight and water content. A suitable water-insoluble PVP polymer is Crosspovidone, sold by GAF Chemicals Corp., which contains about 4% water. These PVP powders are dried at about 105° C. in vacuo for about 2 hours to reduce the water content to less than about 1%.

The dried PVP powders then are suspended at about 5°–10° C. under agitation in a substantial quantity of an anhydrous organic solvent, such as a carboxylic acid ester, a dialkyl ether, e.g. t-butyl methyl ether, or a hydrocarbon e.g. hexane or cyclohexane. Preferably an alkyl or cycloalkyl ester of a saturated aliphatic carboxylic acid is used, as for example, ethyl acetate, propyl acetate, isopropyl acetate, butyl acetate and ethyl propionate. Ethyl acetate is preferred.

A 70–85% aqueous $H_2O_2$ solution then is added to the cooled PVP suspension under continued agitation during a period of about 30 minutes to about 1 hour. The amounts of PVP starting material and $H_2O_2$ solution used correspond to the desired molar ratio of PVP and $H_2O_2$ in the complex. Preferably, however, a small excess of the $H_2O_2$ solution over the desired stoichiometric ratio is used. This excess $H_2O_2$ is recoverable from the mother liquor.

Upon mixing the PVP and $H_2O_2$, a uniform, free-flowing, fine, white powder precipitate is obtained which is filtered and dried at about 40°–50° C. in vacuo to remove residual solvent and water. The product is a stable, anhydrous complex in the form of a uniform, free-flowing, fine, white powder having a $H_2O_2$ content between about 18 and 22% $H_2O_2$. The water content of the product generally is about 2% or less, and usually can be dried to less than about 1%.

Continued drying under these low temperature and vacuum conditions reduces the final water content in the complex to a substantially anhydrous powder with no loss of $H_2O_2$.

EXAMPLE 1

Preparation of Free-Flowing, Fine, White Powders of PVP-H$_2$O$_2$ Complex

PVP-CI (K-30) (GAF Corporation) (4.5% water) was dried at 105° C. in vacuo for 2 hours until it contained only 1.1% water. 160 g. of the dried, water-insoluble PVP was suspended in 450 g. of anhydrous ethyl acetate (0.01% water), and the suspension was cooled to 5°-10° C. while agitating the suspension. Then 55 ml. of 70% hydrogen peroxide solution in water (71 g. H$_2$O$_2$) was added slowly over a period of 35 minutes to the agitated suspension keeping the temperature at 5°-10° C. A fine, white precipitate was formed which was filtered to yield 312 g. of a wet product which was dried at 40°-50° C. in vacuo for 4 hours. 200 g. of a free-flowing fine, white powder was obtained which contained 19.5% H$_2$O$_2$ and 2.9% water. Further drying under the same conditions for an additional 6 hours reduced the water content to 0.5% while maintaining the H$_2$O$_2$ content at 18.5% and without affecting the physical properties of the powder.

In the drying step above, 77.9 g. of mostly ethyl acetate was collected in the vacuum trap which also contained 0.2% H$_2$O$_2$ and 3.78% water in the upper layer and 8.0 g. of mostly water (92%) with 0.63% H$_2$O$_2$.

The filtrate (363 g.) obtained above contained 2.75% H$_2$O$_2$ and 1.54% H$_2$O, the rest being ethyl acetate, which was recycled as described in Example 2 below.

EXAMPLE 2

The procedure of Example 1 is followed using PVP-CI 160 g.; ethylacetate 450 g.; and 85% H$_2$O$_2$ 56 g. 197 g. of a PVP-H$_2$O$_2$ complex with 19.2% H$_2$O$_2$ containing 1.56% H$_2$O is obtained. Further drying at 40°-50° C. in vacuo will reduce the water content to 0.5% H$_2$O.

EXAMPLE 3

Preparation of Free-Flowing, Fine, White Powders of PVP-H$_2$O Complex by Recycling the Filtrate of Example 1

To the filtrate from Example 1, 363 g., was added 90 g. of fresh, anhydrous ethyl acetate followed by cooling to 5°-10° C. Then 170 g. of dried PVP-CI was added at once whereupon the exothermic reaction increased the temperature to 12° C. The suspension was cooled to 5° C. with an ice-water bath. Then 58 g. of a 70% H$_2$O$_2$ solution was added over a period of 2 hours with good agitation. a fine, white precipitate was formed and filtered to provide 320 g. of a wet cake which was dried at 40°-50° C. under vacuo for 4 hours to yield 202 g. of a free-flowing, fine, white powder containing 18.9% H$_2$O$_2$ and 3.1% H$_2$O. Further drying under the same conditions for an additional 6 hours lowered the water content to 0.6%, and the H$_2$O$_2$ content to 18.3%, without affecting the physical characteristics of the powder.

The filtrate weighed 358 g., and was mostly ethyl acetate with 2.58% H$_2$O$_2$ and 1.49% water.

COMPARATIVE EXAMPLE 1

Preparation of Aqueous PVP-H$_2$O$_2$ Complex according to U.S. Pat. No. 3,480,557

To 6 g. of PVP-CI (K-30) (GAF Corporation) (4.5% water) was dissolved in 50 ml. of methanol was added 7 g. of a solution of H$_2$O$_2$ in water (50%), followed by heating at 45° C. for 2 hours, and evaporation of methanol for 12 hours. The gummy, amorphous residue contained 12.92% H$_2$O$_2$ and 5% H$_2$O.

EXAMPLE 4

Stability of Anhydrous Complex of Example 1

After 43 days at 60° C. the complex lost only 15% of its H$_2$O$_2$ activity, which shows excellent stability toward decomposition. At room temperature, decomposition was only 1.5% after 60 days.

EXAMPLE 5

Stability of Aqueous Solutions of Anhydrous Complex of Example 1

An aqueous solution of the complex of Example 1 containing 3.75% H$_2$O was heated at 58° C. for 96 hours. At the end of this period, the solution analyzed for 2.75% H$_2$O, which indicated excellent stability for aqueous solutions of the complex of the invention.

COMPARATIVE EXAMPLE 2

Stability of Aqueous Solutions of (a) Urea/H$_2$O$_2$ and (b) H$_2$O$_2$ (a) Under the same conditions as in Example 5, a urea/H$_2$O$_2$ solution, after only 36 hours, was reduced in H$_2$O$_2$ content from 3.5% to 0.6% H$_2$O$_2$ (b) An H$_2$O$_2$ solution itself lost all of its 3.0% H$_2$O$_2$ content after 36 hours.

It is to be understood that the above examples are provided to illustrate specific and preferred embodiments of the invention and that many modifications and alterations can be made in these examples without departing from the scope of the invention.

What is claimed is:

1. A suspension process for preparing uniform, free-flowing, fine, white powders of a complex of PVP and H$_2$O$_2$ having an H$_2$O$_2$ content between about 18 and about 22% H$_2$O$_2$ and about 2% water or less which comprises:
   (a) forming a suspension of water-insoluble PVP containing less than about 1% water in anhydrous ethyl acetate;
   (b) slowly adding an aqueous H$_2$O$_2$ solution containing about 70 to about 85% by weight H$_2$O$_2$, the amounts of PVP and H$_2$O$_2$ corresponding substantially to the desired molar ratio of PVP and H$_2$O$_2$ in the complex, at a temperature of about 0°-10° C., under agitation, to precipitate a PVP-H$_2$O$_2$ complex in the form of a uniform, free-flowing, fine, white powder,
   (c) filtering, and
   (d) drying the web precipitate with substantially no loss of H$_2$O$_2$ to form the desired powders having the improved properties defined above.

2. A process according to claim 1 wherein the filtrate is recycled for use in step (a).

3. A process according to claim 1 wherein drying is carried out at about 50°-60° C. in vacuo.

4. A process according to claim 1 wherein said complex contains about 1% water or less.

5. A process according to claim 1 wherein said H$_2$O$_2$ solution contains about 70% H$_2$O$_2$.

6. A process according to claim 1 wherein said H$_2$O$_2$ solution contains about 85% H$_2$O$_2$.

* * * * *